US006173204B1

(12) United States Patent
Sullivan et al.

(10) Patent No.: US 6,173,204 B1
(45) Date of Patent: Jan. 9, 2001

(54) SEMICONDUCTOR ASSISTED RELAY IN A BIPHASIC DEFIBRILLATOR

(75) Inventors: Joseph L. Sullivan; Lawrence A. Borschowa, both of Kirkland, WA (US)

(73) Assignee: Physio-Control Manufacturing Corporation, Redmond, WA (US)

( * ) Notice: Under 35 U.S.C. 154(b), the term of this patent shall be extended for 0 days.

(21) Appl. No.: 09/170,860

(22) Filed: Oct. 13, 1998

(51) Int. Cl.[7] ..................... A61N 1/39
(52) U.S. Cl. ..................... 607/5
(58) Field of Search ..................... 607/5

(56) References Cited

U.S. PATENT DOCUMENTS

| | | | |
|---|---|---|---|
| 4,077,413 | 3/1978 | Partridge . | |
| 4,850,357 | 7/1989 | Bach, Jr. . | |
| 5,083,562 | 1/1992 | de Coriolis et al. . | |
| 5,199,429 | 4/1993 | Kroll et al. . | |
| 5,395,394 | 3/1995 | Cameron | 607/5 |
| 5,443,490 | 8/1995 | Flugstad . | |
| 5,507,781 | 4/1996 | Kroll et al. . | |
| 5,514,160 | 5/1996 | Kroll et al. . | |
| 5,534,015 | 7/1996 | Kroll et al. . | |
| 5,591,209 | 1/1997 | Kroll . | |
| 5,593,427 | 1/1997 | Gliner et al. . | |
| 5,601,612 | 2/1997 | Gliner et al. | 607/7 |
| 5,607,454 | 3/1997 | Cameron et al. . | |
| 5,620,470 | 4/1997 | Gliner et al. . | |
| 5,674,266 | 10/1997 | Stendahl . | |
| 5,769,872 * | 6/1998 | Lopin et al. | 607/5 |
| 5,797,968 | 8/1998 | Lopin et al. . | |
| 5,803,927 * | 9/1998 | Cameron et al. . | |
| 5,824,017 * | 10/1998 | Sullivan et al. | 607/5 |
| 5,891,172 * | 4/1999 | Stendahl et al. | 607/5 |

FOREIGN PATENT DOCUMENTS

| | | |
|---|---|---|
| 598617 | 5/1994 | (EP) . |

* cited by examiner

*Primary Examiner*—Carl H. Layno
(74) *Attorney, Agent, or Firm*—Christensen O'Connor Johnson Kindness PLLC

(57) ABSTRACT

An external defibrillator for applying a multiphasic defibrillation pulse to a patient uses a single semiconductor switching element in combination with a relay switching element. The semiconductor switching element is used to stop the flow of current from the energy storage device to the patient in between the phases of the multiphasic defibrillation pulse. The relay element is used to switch the leads of the energy storage device so as to create the different phases of the multiphasic defibrillation pulse. In various examples, the relay element is shown to be in the form of: a double-pole, double-throw relay; two single-pole, double-throw relays; or four reed relays. The timing between the activation of the semiconductor switching element and the relay switches may be delayed, so as to give the relatively slower relay switches time to respond. In the embodiment utilizing the two single-pole, double-throw relays, in the resting positions the relays may be coupled to the same terminal of the energy storage device, and a pair of diodes may be used so as to prevent short circuiting of a defibrillation pulse from a second defibrillator.

28 Claims, 6 Drawing Sheets

SEMICONDUCTOR ASSISTED RELAY IN A BIPHASIC DEFIBRILLATOR

FIELD OF THE INVENTION

This invention relates to output circuits in cardiac defibrillators and, more specifically, to an output circuit utilizing a low-cost relay as part of the capacitor switching circuitry of a biphasic defibrillator.

BACKGROUND OF THE INVENTION

One of the most common and life-threatening medical conditions is ventricular fibrillation, a condition in which the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. Different switching mechanisms may be used depending in part on whether the defibrillator applies a monophasic or multiphasic defibrillation pulse to the patient. A discharge control signal causes the switching mechanism to complete an electrical circuit between the storage capacitor and the defibrillator output terminals that are connected to the electrodes attached to the patient.

One prior art circuit that uses relatively expensive semiconductor switching elements in an output circuit to deliver biphasic defibrillation pulses is shown in FIG. 1A. FIGS. 1A and 1B are taken from prior art U.S. Pat. No. 5,083,562 to de Coriolis et al. FIG. 1A shows four relatively expensive semiconductor switching elements 40, 42, 44, and 46, which are used to deliver the energy from a large storage capacitor 39 to a patient's heart 18. As shown, when the switches 40 and 42 are closed, the energy flows from the capacitor 39 through the heart 18 in the downward direction, as indicated by arrow 68. To accomplish the second phase of the biphasic pulse, switches 40 and 42 are opened and the switches 44 and 46 are closed, thus causing the remaining energy from the capacitor 39 to flow through the heart 18 in the upward direction, as indicated by arrow 70.

The biphasic pulse that is produced by the circuit of FIG. 1A is shown in FIG. 1B. As can be seen in FIG. 1B, during the first phase of the biphasic pulse when the switches 40 and 42 are closed, the voltage on the storage capacitor 39 drops from V1 to V2. Then, when the switches 40 and 42 are opened and the switches 44 and 46 are closed, the energy storage capacitor 39 is essentially flipped over, causing the remaining voltage V2 on the storage capacitor to be essentially referenced as negative voltage. The negative voltage V2 then flows through the heart as the second phase of the biphasic pulse until the voltage level reaches V3, at which time switch 48 is closed to discharge the remaining energy from the storage capacitor 39.

FIGS. 2A and 2B are taken from prior art U.S. Pat. No. 5,468,254 to Hahn et al. FIG. 2A shows a similar circuit to that of FIG. 1A in that it also uses four semiconductor switches. In the circuit of FIG. 2A, two of the switches are shown to be SCRs (semiconductor- or silicon-controlled rectifiers) while the remaining two switches are shown merely to be electronic. Given the large voltages and currents used in defibrillators, the most commonly used semiconductor switching elements are SCRs and IGBTs (insulated gate bipolar transistors). FIG. 2B shows the biphasic pulse produced by the circuit of FIG. 2A.

Defibrillators such as those shown in FIGS. 1A and 2A, which apply a biphasic pulse and use semiconductor switching elements, are relatively new in the art of defibrillators. Older defibrillators usually applied only a monophasic pulse and used low-cost relays rather than the more expensive semiconductor switching elements. The reason the low-cost relays are generally thought to be incapable of use in the newer biphasic defibrillators is due to the fact that the low-cost relays are unable to be controlled with the precision required for biphasic defibrillation pulses. More specifically, when the switching elements of a relay are physically opened, energy tends to arc or spark across the relay if the voltages or currents are too high. High voltages and currents are especially present in external defibrillators that are designed to apply a defibrillation pulse to a patient externally through the patient's skin and chest (wherein more tissue causes greater resistance). This is in contrast to internal defibrillators that are surgically implanted into a patient so as to conduct the energy directly to the patient's heart tissue (wherein less tissue means less resistance). The arcing problems of relays do not generally occur with semiconductor switching elements that, unlike relays, do not have any moving metal parts and so do not have the same arcing or sparking problem.

The arcing phenomenon is especially problematic in biphasic defibrillators that, as described above, have to stop the flow of high energy in between the first and second phases of a biphasic pulse. If a simple conventional relay is used in a biphasic defibrillator to break the energy flow, the energy may arc across the relay. In addition to wearing out the relay, this arcing would drain the capacitor of its remaining energy that is supposed to be used for the second phase of the defibrillation pulse. Thus, the potentially life-saving second phase of the defibrillation pulse would be eliminated. Again, this is not an issue in monophasic defibrillators, because they only deliver one pulse that uses almost all of the energy of the storage capacitor. The monophasic defibrillators do not try to stop the high energy flow during the capacitor discharge when such an interruption is more likely to result in arcing or sparking.

The present invention is directed to providing an apparatus that overcomes the foregoing and other disadvantages. More specifically, the present invention is directed to providing an output circuit for a biphasic defibrillator that reduces the number of expensive semiconductor switches that are used.

SUMMARY OF THE INVENTION

An external defibrillator having an output circuit that allows a biphasic defibrillation pulse to be applied to a patient from an energy storage device is disclosed. The output circuit includes a number of switches and a pair of output terminals. By selectively switching the switches of the output circuit, the energy storage device may be selectively coupled to the patient so as to apply a multiphasic defibrillation pulse.

In accordance with one aspect of the invention, the switches of the output circuit include at least one semiconductor switching element and a relay circuit. The semiconductor switching element is used to stop the flow of energy in between the phases of the biphasic defibrillation pulse. More specifically, the semiconductor switching element stops the flow of current from the energy storage device to the patient so as to end the first phase of the multiphasic defibrillation pulse. Once the current flow is stopped by the semiconductor switching element, the relay circuit is able to switch the leads of the energy storage capacitor so that the second phase of the multiphasic defibrillation pulse may begin. The use of a single semiconductor switching element in combination with a low-cost relay reduces the cost and complexity of the output circuit in comparison with an implementation using several semiconductor switching elements. In addition, by using a semiconductor switching element in the current path, additional phases of the defibrillation pulse can easily be added by simply switching the semiconductor switch at additional times. This is in contrast to an implementation using SCR switches in an H-bridge configuration, which may drain the capacitor completely during the second phase of the defibrillation pulse.

In accordance with yet another aspect of the invention, the relay circuit includes a plurality of relay switches that selectively couple the first and second leads of the energy storage device to the first and second output terminals of the output circuit. More specifically, once the control circuit moves the relay switches to a first set of positions, the relay switches electrically couple the first lead of the energy storage capacitor to the first output terminal, and also electrically couple the second lead of the energy storage capacitor to the second output terminal. Then, when the control circuit moves the relay switches to a second set of positions, the relay switches electrically couple the first lead of the energy storage capacitor to the second output terminal, and also electrically couple the second lead of the energy storage capacitor to the first output terminal. The first and second sets of positions of the relay switches correspond to the first and second phases of the multiphasic defibrillation pulse, respectively.

In accordance with yet another aspect of the invention, the control circuit that generates the control signals for the semiconductor switching element and the relay switches generates the control signals for the relay switches slightly before generating the control signals for the semiconductor switching element. In other words, because the semiconductor switching element may respond more quickly to the control signals than the relay switches, the control signal for the relay switches may be activated slightly ahead of time, so as to reduce the delay between when the semiconductor switching element and the relay switches respond to the control signals.

In accordance with still another aspect of the invention, the relay circuit may include any of several types of relay switches. In various embodiments, the relay switches may, for example, be: a single double-pole, double-throw relay switch; two single-pole, double-throw relay switches; or four reed relay switches. In the embodiment using the two single-pole, double-throw relays, the normally closed position of the relays is set so that the switches are switched to the same lead of the energy storage capacitor, and two additional diodes are placed with their anodes toward the relay switches and their cathodes toward the output terminals. In this configuration, the diodes stand off the voltage from a second defibrillator, rather than short-circuiting a defibrillation pulse from the second defibrillator. This configuration also helps prevent leakage currents to the patient. For similar reasons, in the embodiment using four reed relays, the normal resting positions of the four reed relays are set so that the relays are open and thus electronically isolated, so as to prevent the short circuiting of a defibrillation pulse from a second defibrillator. This configuration also prevents leakage currents to the patient and can improve preamplifier performance by isolating the preamplifier inputs from the other circuit components.

It will be appreciated that the disclosed output circuit is advantageous in that by combining a low-cost relay with a single semiconductor switch, a relatively inexpensive output circuit is produced that is capable of effectively applying a multiphasic defibrillation pulse to a patient. The use of the semiconductor switching element to stop the flow of current between the phases of the defibrillation pulse allows the use of the low-cost relay to accomplish the switching of the energy storage device. In addition, the use of diodes and/or specific resting switching positions for the relay switches allows the output circuit to prevent the short circuiting of a defibrillation pulse from a second defibrillator, and to inhibit leakage currents that would otherwise be applied to the patient.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 3:
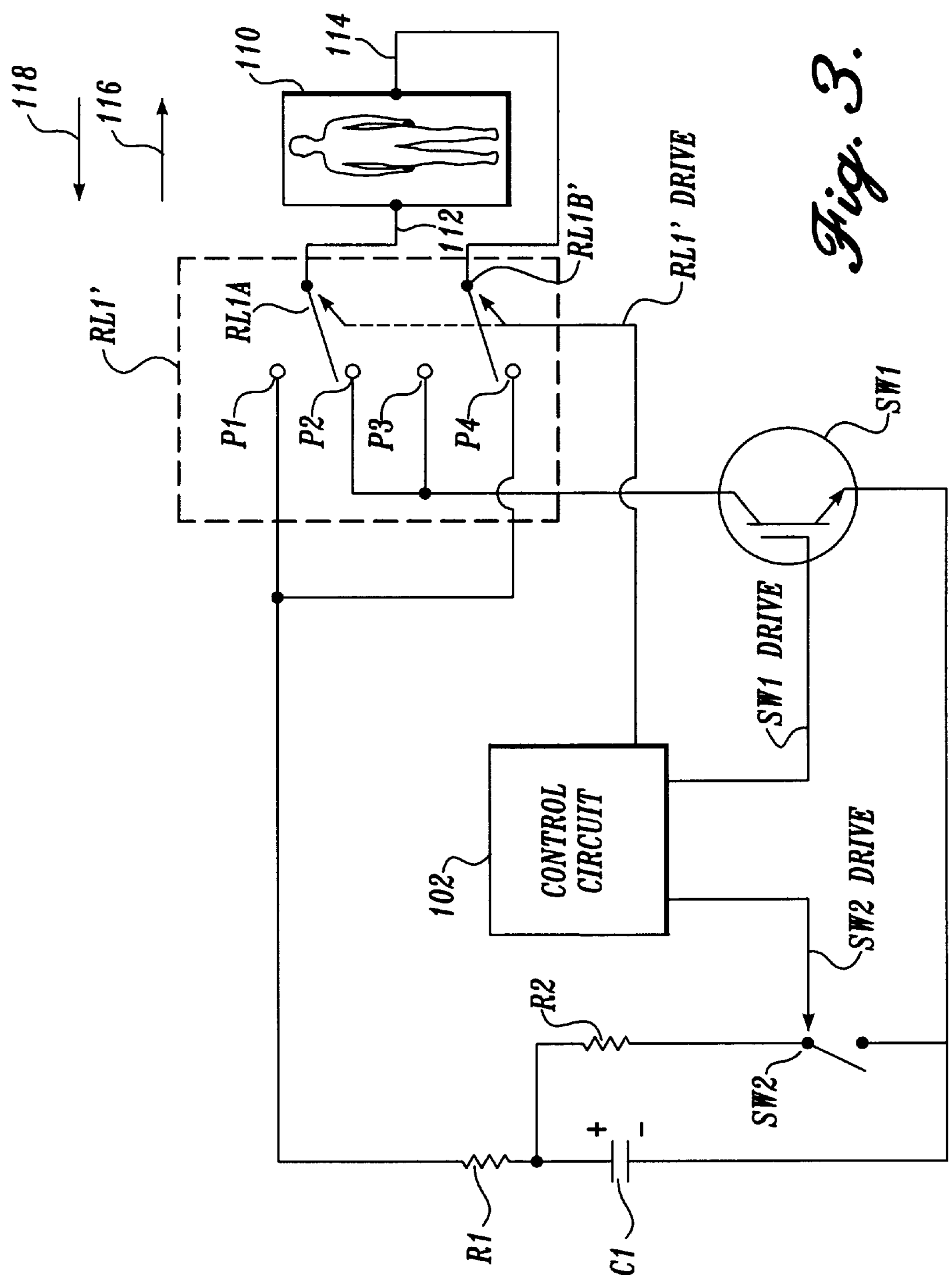
FIG. 3 is a schematic diagram of an output circuit formed according to the present invention utilizing a low-cost relay and a single semiconductor switch.

FIG. 3 illustrates a first embodiment of the invention using a low-cost relay RL1'. Relay RL1' is a double-pole, double-throw (DPDT) relay, with the double-throw relay switches being designated as RL1A and RLIB. Relay switch RL1A connects the apex line 112 from the patient 110 to either pole P1 or P2. The second relay switch RL1B connects the sternum line 114 from the patient 110 to either pole P3 or P4. Switching element SW1 is an IGBT (insulated gate bipolar transistor). In an actual embodiment, switching element SW1 is comprised of two IGBTs in series. In addition, a dump circuit consisting of a resistor R2 and a switch SW2 is connected in parallel with capacitor C1 for dumping unwanted energy from the capacitor C1. A control circuit 102 controls relay RL1' with a RL1' drive signal, and controls switch SW1 with an SW1 drive signal, and also controls switch SW2 with an SW2 drive signal. Poles P1 and P4 are coupled through a protective element R1 to the positive terminal of an energy storage capacitor C1. Poles P2 and P3 are coupled through IGBT switch SW1 to the negative terminal of energy storage capacitor C1. Protective element R1 is a resistor that provides short circuit protection by limiting the current from the capacitor C1 in the event of a short circuit. In alternate embodiments, rather than a resistor R1, an IGBT desaturation detector could be used in combination with the IGBT switch SW1, or a high frequency patient impedance sensing method could be used. Since the resistor R1 is a protective component, its inclusion is not strictly required for circuit operation.

Figure 1A:
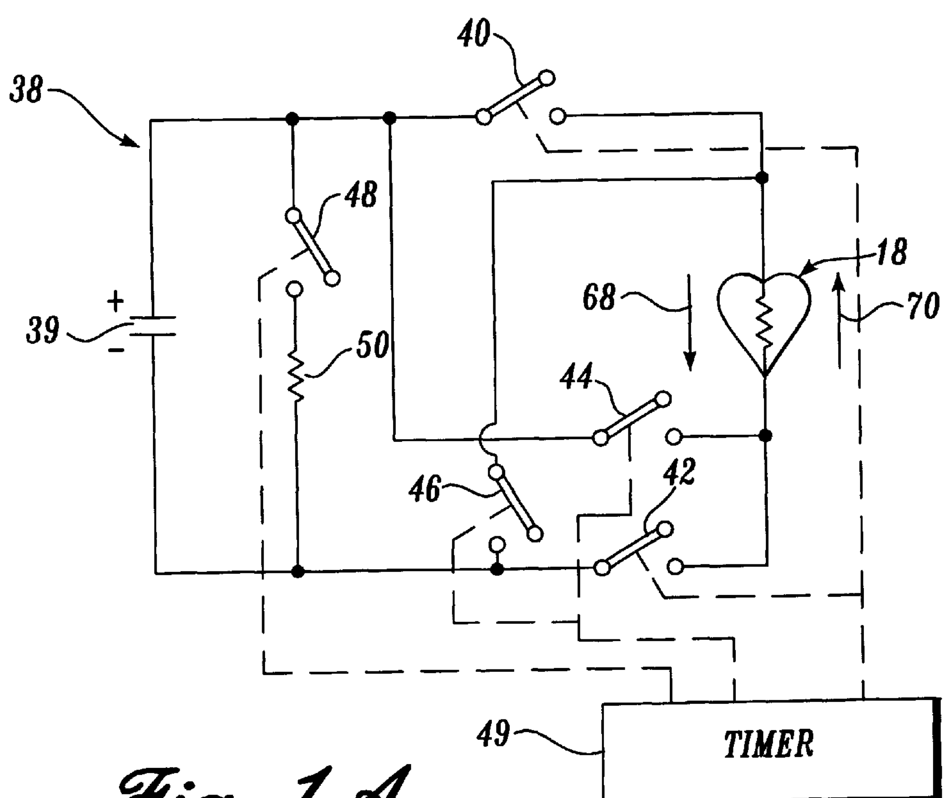
FIG. 1A is a schematic diagram of a prior art H-bridge circuit in a defibrillator for applying a biphasic defibrillation pulse to a patient's heart.
Figure 1B:
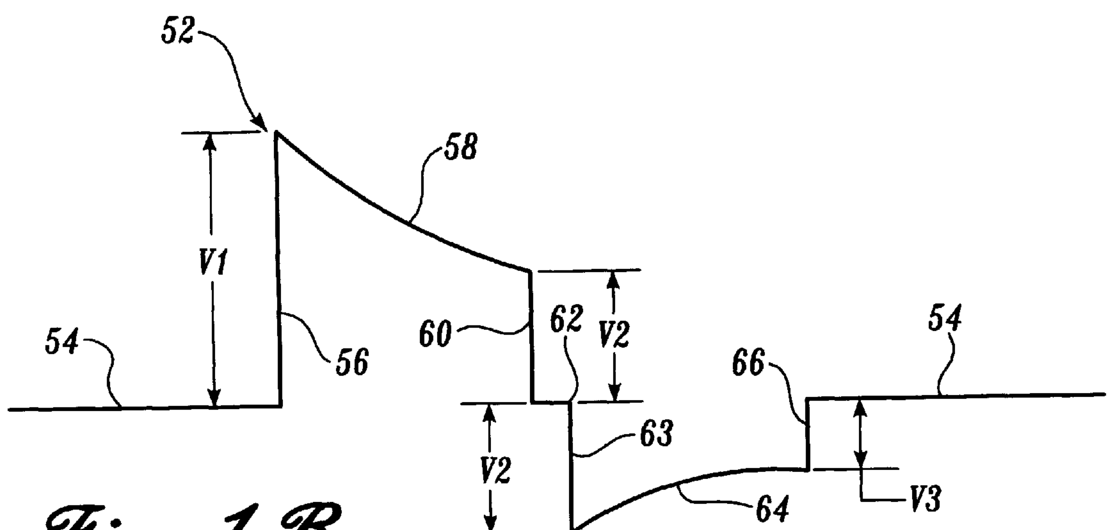
FIG. 1B is a timing diagram illustrating the operation of the prior art circuitry of FIG. 1.
Figure 2A:
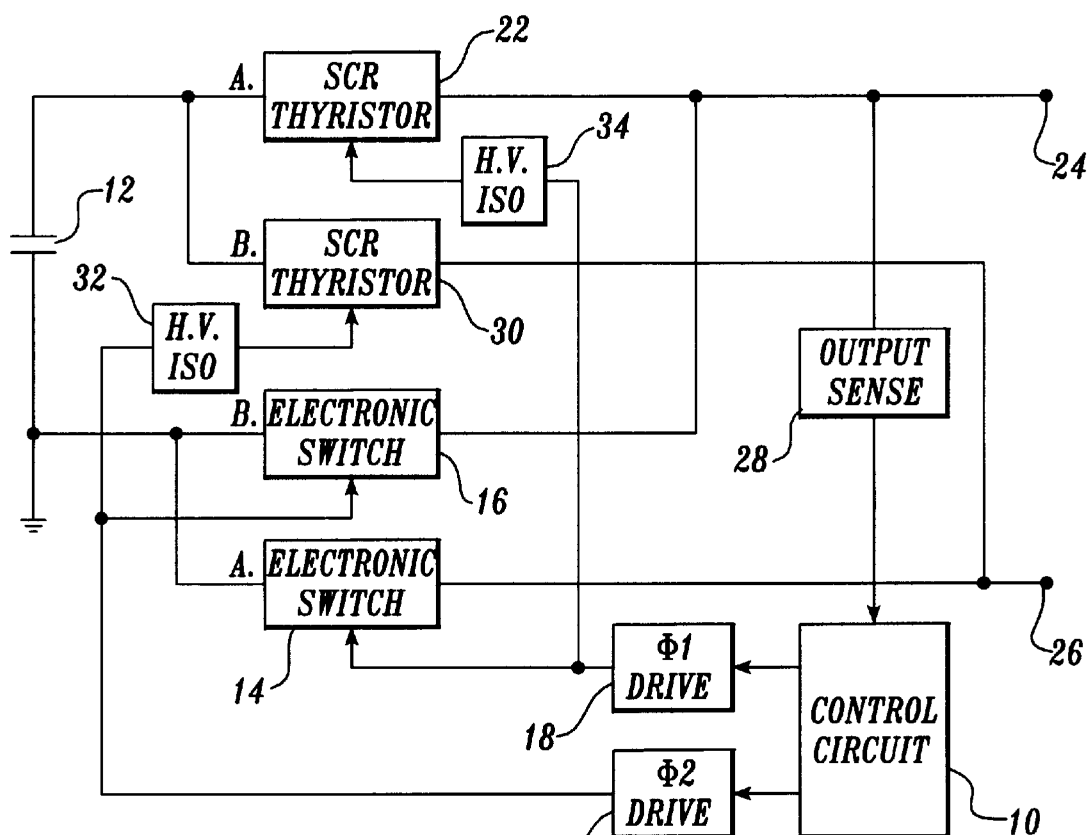
FIG. 2A is a schematic diagram of another prior art H-bridge circuit for applying a biphasic defibrillation pulse to a patient's heart.
Figure 2B:
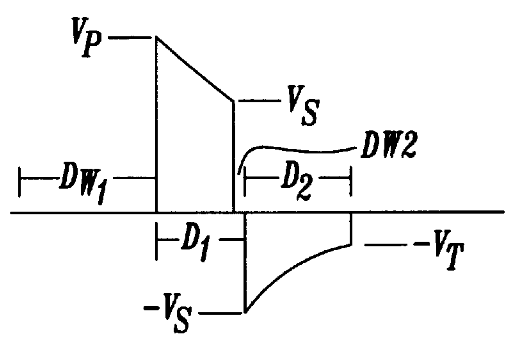
FIG. 2B is a timing diagram illustrating the operation of the prior art circuitry of FIG. 2A.

When the relay switches RL1A and RLIB switch to poles P1 and P3, respectively, and the switch SW1 is made conducting, energy from the storage capacitor C1 flows through the patient 110 in the left-to-right direction, as indicated by arrow 116. When the relay switches RL1A and RLL1B are connected to the poles P2 and P4, respectively, and the switch SW1 is made conducting, the energy from the storage capacitor CI flows through the patient 110 in the right-to-left direction, as indicated by arrow 118. The biphasic defibrillation pulse that is created is illustrated in FIG. 4 and is similar to the waveforms in FIG. 1B and 2B.

Figure 4:
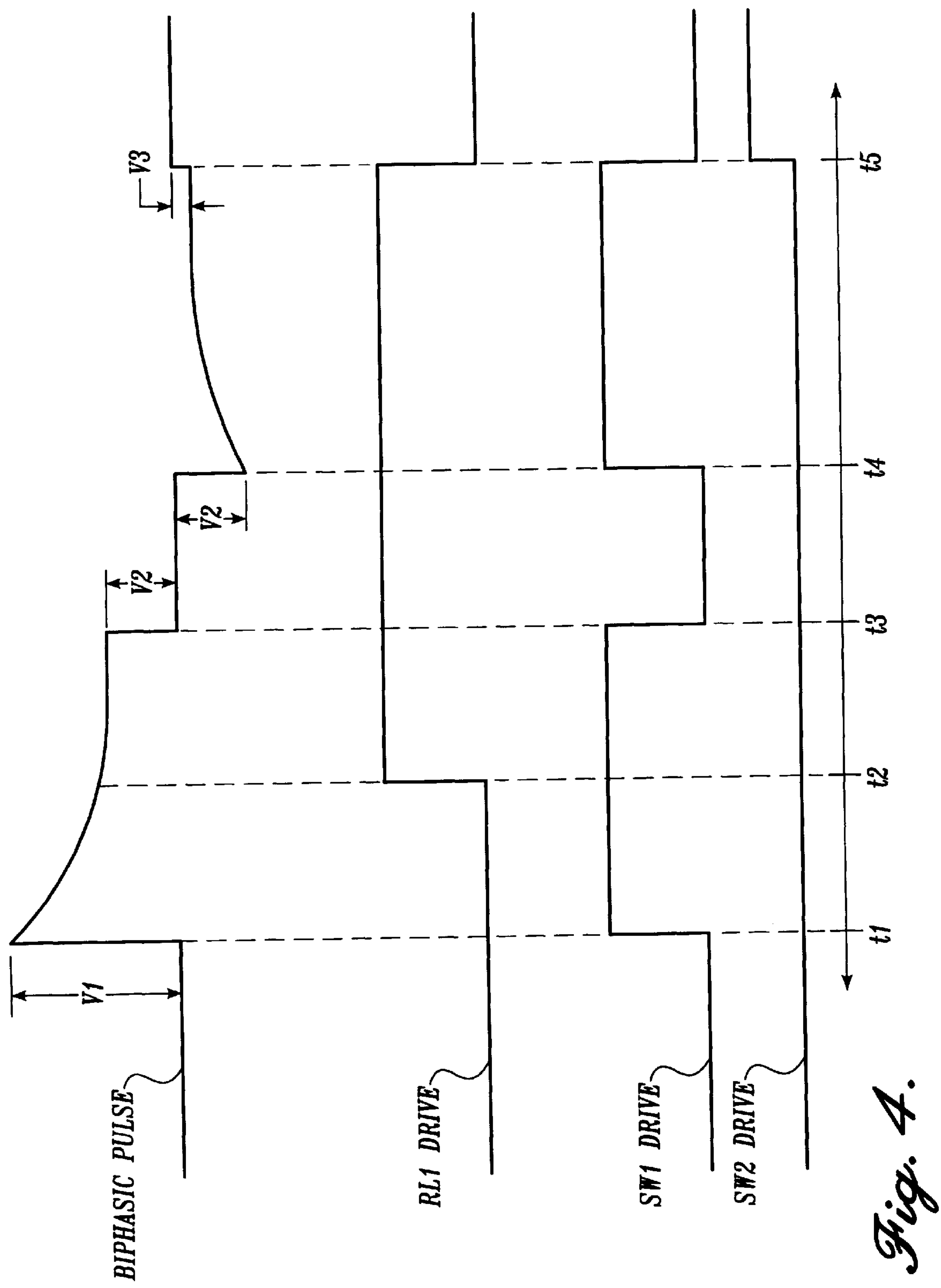
FIG. 4 is a sequence of timing diagrams illustrating the operation of the circuit of FIG. 3.

FIG. 4 shows a timing diagram for a biphasic defibrillation pulse and some timing signals for controlling the relay RL1', the IGBT switch SW1, and dump switch SW2 of FIG. 3. As described previously, the timing signals are generated by the control circuit 102, which may include a microprocessor or other suitably programmable computer. As can be seen from the defibrillation pulse timing diagram, the first phase of the defibrillation pulse starts at time t1 and ends at time t3 when switch SW1 is made non-conducting. From time t3 to time t4, a pause occurs during which the relay switching elements RL1A and RL1B are switched so as to essentially flip the capacitor C1 over. At time t4, the second phase of the biphasic defibrillation pulse begins when the switch SW1 is made conducting again and continues until time t5 when the waveform is truncated by means such as closing the switch SW1 and/or using the dump circuit of resistor R2 and switch SW2. If additional phases of a multiphasic defibrillation pulse were desired, at time t5, rather than switching switch SW2, switch SW1 could again be made non-conducting, after which the process of the first phase could be repeated.

The primary advantage of the implementation illustrated in FIG. 3 is that the four expensive semiconductor switching elements, such as SCRs and IGBTs that are found in most prior art biphasic circuits, have been replaced with a single semiconductor switching element (SW1) and a low-cost double-pole, double-throw relay element (RL1'). Relay RL1' by itself would not be controllable to stop the delivery of energy from the capacitor C1 between the biphasic pulses because it would tend to arc and drain the remaining energy from the capacitor. By combining the low-cost relay RL1' with a single semiconductor switch SW1 as is done in the invention, the delivery of the energy from the capacitor C1 is stopped by the semiconductor switch SW1 with the precision that is desired for stopping the energy flow between phases, while the low-cost relay RL1' accomplishes the switching of the capacitor. In this way, three of the expensive semiconductor switching elements of the prior art circuits are replaced with a single, much less expensive double-pole, double-throw relay.

One of the inventive parts of the timing diagrams in FIG. 4 involves the action of the relay RL1' drive signal between the times t1 and t3. In an ideal system, the relay RL1' would respond instantly to its drive signal and thus the relay RL1' drive signal would not need to transition upward until time t3. However, in an actual embodiment, the relay RL1' has certain delays associated with it. To compensate for this, the invention causes the relay RL1' drive signal to transition slightly before the time actually desired for switching the relay. More specifically, the relay RL1' drive signal is transitioned early at time t2. While the relay RL1' drive signal is transitioned at time t2, the delay associated with the relay RL1' causes the actual switching in the relay to take place some time between times t3 and t4. If the relay RL1' drive is not transitioned early at time t2, the pause between the two phases of the biphasic defibrillation pulse, i.e., between t3 and t4, would need to be lengthened while the circuit waited for the relay switches RL1A and RL1B to finish switching. The specific lead time for transitioning the relay RL1' drive signal depends on a number of factors, such as the relay specifications that are dependent on how the relay is being used and the electrical parameters under which the switching is occurring. By transitioning the relay RL1' drive signal early, the pause between the times t3 and t4 is shortened. For purposes of illustration only, if a relay were of a type for which there was between a 5 to 10 ms delay in switching, and it were known that part of that was due to a 5 ms delay while the electromagnetic field of the relay was charging before the armature began to move, then the relay drive signal could be sent 5 ms early so as to shorten the delay time from a range of 5 to 10 ms to a range of 0 to 5 ms, thus also shortening the delay between the phases of the defibrillation pulse. Such a shortened pause is important, because too long of a pause between the biphasic pulses can endanger the patient. More specifically, it has been experimentally determined that in some cases the waveform efficacy may begin to be reduced if the pause between the phases exceeds somewhat longer than 5 ms, although in some cases longer pauses may be acceptable. In addition, it is desirable to have the relay switches finish transitioning before the switch SW1 switches, in order to avoid the arcing problem described earlier.

Figure 5:
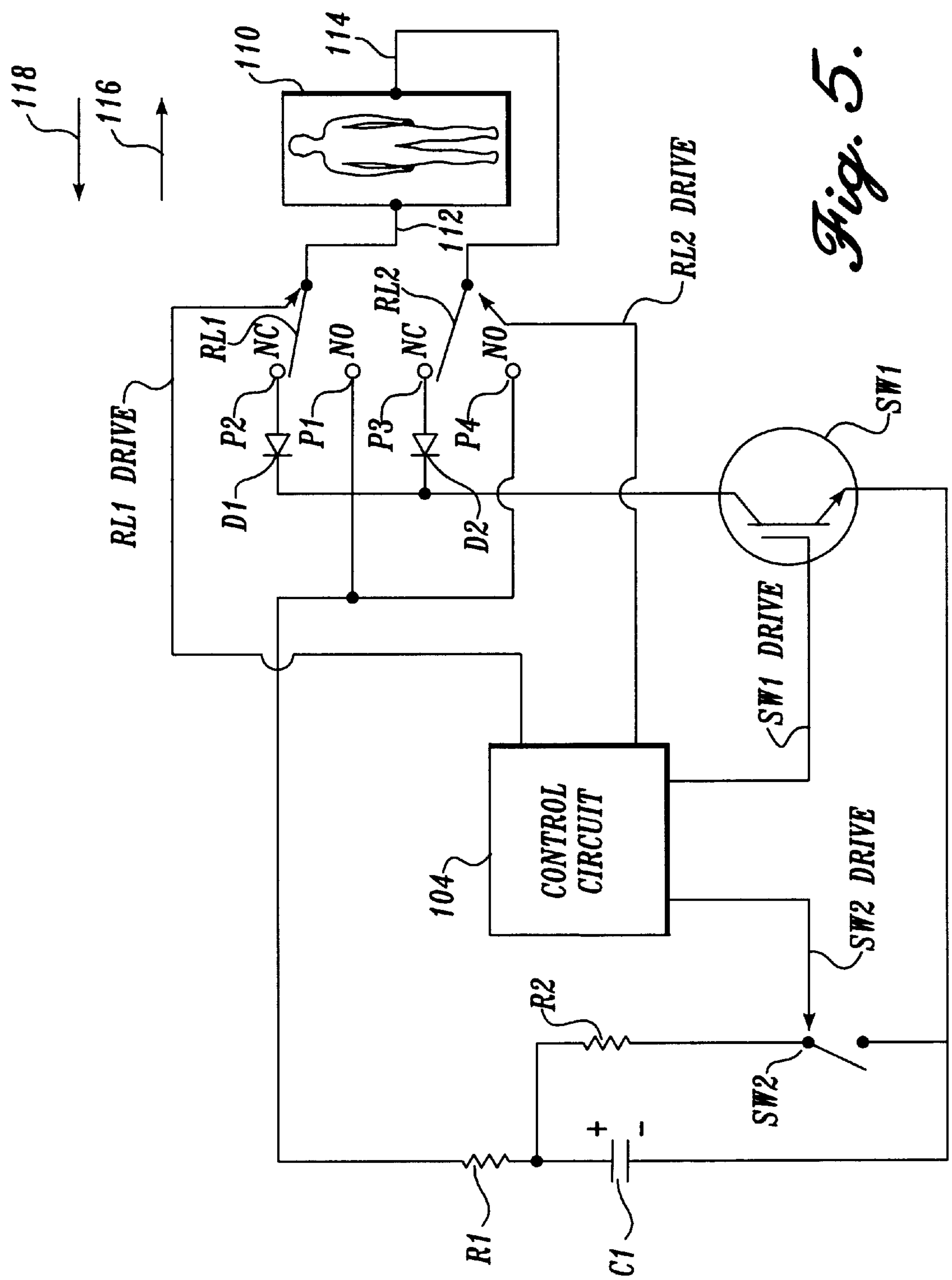
FIG. 5 is a schematic diagram of an alternate embodiment of the present invention utilizing two low-cost relays and a single semiconductor switch.

FIG. 5 illustrates an alternate embodiment of the circuit shown in FIG. 3. Rather than using one double-pole, double-throw relay, the circuit of FIG. 5 uses two single-pole, double-throw (SPDT) relays. The two relays shown in FIG. 5 are designated as relays RL1 and RL2. Relay RL1 connects the apex line 112 from the patient 110 to either pole P1 or P2. Relay RL2 connects the sternum line 114 from the patient 110 to either pole P3 or P4. Poles P1 and P4 are coupled through a resistor R1 to the positive terminal of capacitor C1, while poles P2 and P3 are coupled through IGBT switch SW1 to the negative terminal of capacitor C1. A diode D1 has its anode coupled to pole P2 and its cathode coupled to the drain of switch SW1, while a diode D2 has its anode connected to pole P3 and its cathode connected to the drain of switch SW1. As described in more detail below, the purpose of the diodes D1 and D2 is to prevent current flow from a second defibrillator that may be attached to the patient at the same time as the circuit of FIG. 5. A dump circuit consisting of a resistor R2 and a switch SW2 is connected in parallel with a capacitor C1. A control circuit 104 controls relays RL1 and RL2, as well as switches SW1 and SW2.

One problem that can occur in defibrillators is the short circuiting of a defibrillation pulse from a simultaneously attached second defibrillator. In other words, the situation may sometimes occur where once a first defibrillator is connected to a patient in an emergency situation by a first emergency response team, a second defibrillator may be connected to the patient at a later time by a second emergency response team while the first defibrillator is still attached. In such a circumstance, the circuitry of the first defibrillator must be able to withstand a shock from the second defibrillator, without breaking down and allowing the defibrillation shock from the second defibrillator to short circuit through the first defibrillator's circuitry rather than being applied to the patient.

To address this problem, as illustrated in FIG. 5 when relays RL1 and RL2 are in their normally closed resting position, relay RL1 is switched to pole P2 and relay RL2 is switched to pole P3. In this position, if a high voltage occurred across the patient due to the application of a defibrillation pulse by a second defibrillator, the diodes D1 and D2 prevent the flow of energy from pole P2 to the pole P3, which would otherwise be a short circuit for the energy from the second defibrillator.

One of the advantages of the two single-pole, double-throw relays used in the embodiment of FIG. 5 is as follows. With reference to FIG. 3, there is no way in a double-pole, double-throw relay to connect two diodes so that they will work as described above with reference to FIG. 5. More specifically, the relay RL1 in FIG. 3 can only occupy two positions (i.e., switch to poles P2 and P4, or else switch to poles P1 and P3). Thus, if the diodes were placed on the legs containing poles P1 and P3, this would prevent normal defibrillator operation, as would placing the diodes on the legs for the poles P2 and P4. In contrast, each of the relays RL1 and RL2 of FIG. 5 are independently controllable. More specifically, the relays RL1 and RL2 can be set for their normally closed resting position to be the poles P2 and P3, respectively. This allows the diodes D1 and D2 to be placed as shown, so as to prevent a second defibrillator from shorting its discharge across the circuit of FIG. 5, while still allowing normal defibrillator operation.

Another problem that can occur in defibrillators is related to leakage currents. Leakage currents are relatively small currents that flow through solid-state devices even when they are supposed to be in the off state. For example, solid-state devices such as SCRs and IGBTs in some applications may have a leakage current of around 1 milliamp. This is because solid-state devices typically rely on gate voltages or similar phenomena to control the current flow. Even with the gate voltages all the way off, a small amount of leakage current usually still results through the semiconductor elements. The IGBT switch SW1 is a solid-state switch through which leakage currents may occur.

To address this problem, as previously described with respect to FIG. 5, when relays RL1 and RL2 are in their normally closed resting position, relay RL1 is switched to pole P2 and relay RL2 is switched to pole P3. In this position, even if IGBT switch SW1 would otherwise be experiencing leakage currents, there is no circuit path between the positive and negative terminals of the capacitor C1, so that no leakage currents flow.

This additional leakage current advantage of the two single-pole, double-throw relays used in the embodiment of FIG. 5 can be described in more detail as follows. With reference to FIG. 3, there is no way in a double-pole, double-throw relay for the switches to be implemented so that leakage currents will not flow, as described above with reference to FIG. 5. More specifically, the relay RL1' in FIG. 3 can only occupy two positions (i.e., switch to poles P2 and P4, or else switch to poles P1 and P3). When the relay RL1' is switched to poles P2 and P4, leakage currents may flow to the patient 10 from the positive terminal of capacitor C1, through resistor R1, through pole P4, back through pole P2 and down through the leaking IGBT switch SW1 to the negative terminal of capacitor C1. When the relay RL1 is switched to poles P1 and P3, leakage currents are able to flow from the positive terminal of the capacitor C1 through resistor R1 through pole P1, back through pole P3, through the leaking IGBT switch SW1 to the negative terminal of capacitor C1. As described above, these paths for leakage current are prevented by the configuration of FIG. 5. More specifically, the relays RL1 and RL2 can be set for their normally closed resting positions to be the poles P2 and P3, respectively, for which the leakage currents are prevented.

The circuit of FIG. 5 performs normal biphasic defibrillator operation in the following manner. The timing for the phases of the biphasic pulse is similar to the timing described with respect to FIG. 4. For the first phase of the biphasic pulse in the circuit of FIG. 5, relay RL1 is switched to pole P1 while relay RL2 remains switched to pole P3, thus allowing energy to flow from the positive terminal of the capacitor C1 through the pole P1 to the patient 110 back through the pole P3 and the switch SW1 to the negative terminal of the capacitor C1. To end the first phase, the IGBT switch SW1 is turned off to stop the energy flow in between the two phases. As described previously with respect to FIG. 4, it may be desirable to transition relays such as RL1 and RL2 slightly before turning off SW1, since relays generally operate slower than an IGBT switch such as switch SW1. For the second phase, relay RL1 switches to pole P2 and relay RL2 switches to pole P4, so that the remaining energy stored by the capacitor C1 can flow from the positive terminal of the capacitor C1 through the pole P4 through the patient, and back through the pole P2 and the switch SW1 to the negative terminal of the capacitor C1. In this manner, by using the two diodes D1 and D2 and the two single-pole, double-throw relays RL1 and RL2, the circuit of FIG. 5 is functional for performing the normal operation of applying a biphasic defibrillation pulse, while still preventing the short circuiting of a second defibrillator, and inhibiting leakage currents.

Figure 6:
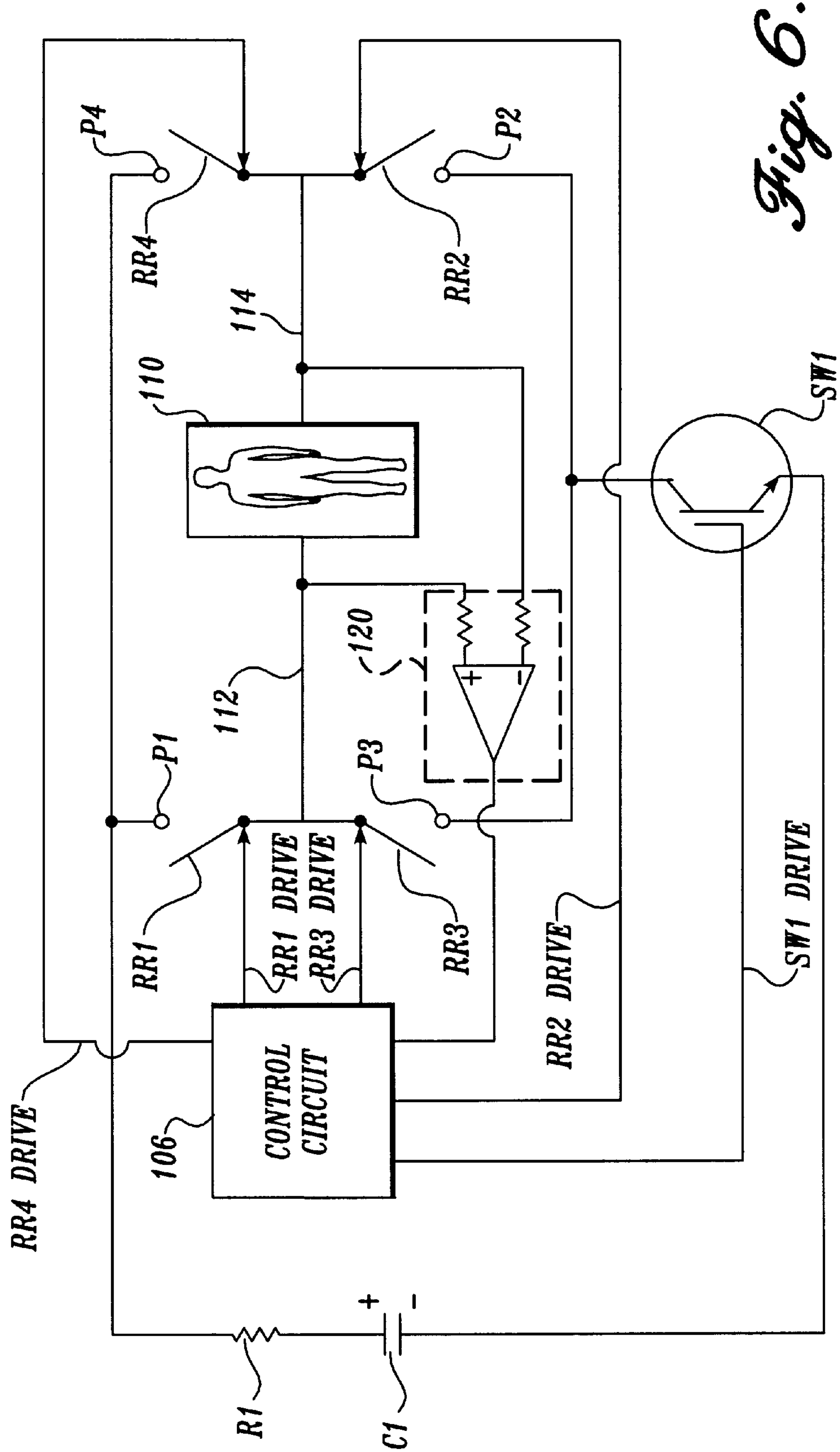
FIG. 6 is a schematic diagram of another alternate embodiment of the present invention utilizing four low-cost relays and a single semiconductor switch.

FIG. 6 shows another alternate embodiment of the output circuit of the present invention. As shown in FIG. 6, four reed relays RR1, RR2, RR3, and RR4 are used to form the circuit for coupling the storage capacitor C1 to the patient 110. Reed relays are one example of a single-pole, single-throw (SPST) relay that can be used. It will be understood that an alternate embodiment may use other types of SPST relays. Reed relay RR1 connects the apex line 112 from the patient 110 to pole P1. Reed relay RR3 connects the apex line 112 from the patient 110 to the pole P3. Reed relay RR2 connects the sternum line 114 from the patient 110 to the pole P2. Reed relay RR4 connects the sternum line 114 from the patient 110 to pole P4. Poles P1 and P4 are coupled through a resistor RI to the positive terminal of energy storage capacitor C1. Poles P2 and P3 are coupled through IGBT switch SW1 to the negative terminal of energy storage capacitor C1. A control circuit 106 controls reed relays RR1–RR4 as well as switch SW1. A preamplifier 120 measures the signals from apex line 112 and sternum line 114 and provides the measurements to the control circuit 106.

In an actual embodiment, a special dump circuit (e.g., resistor R2 and switch SW2 of FIGS. 3 and 5) for dumping unwanted energy from the storage capacitor C1 may not be required in the embodiment of FIG. 6. In other words, by activating reed relays RR1 and RR3, as well as switch SW1 simultaneously, unwanted energy can be dumped from the capacitor C1. Alternatively, reed relays RR2 and RR4, as well as switch SW1, can be activated simultaneously to dump unwanted energy.

The circuit of FIG. 6 performs normal biphasic defibrillator operation in the following manner. The timing for the phases of the biphasic pulse is similar to the timing described with respect to FIG. 4. For the first phase of the biphasic pulse in the circuit of FIG. 6, reed relay RR1 is switched to pole P1, while reed relay RR2 is switched to pole P2, and reed relays RR3 and RR4 are open, and switch SW1 is conductive. This relay configuration allows current to flow from the positive terminal of capacitor C1 through pole P1 to patient 110, back through pole P2, and switch SW1 to the negative terminal of capacitor C1. Because reed relays are being used, when the reed relays RR1 through RR4 are not connected to a given pole, they are electrically isolated from the poles. As described previously with respect to FIG. 4, it may be desirable to transition the relays early, since their operation is generally slower than that of IGBT switch SW1. To end the first phase, the IGBT switch SW1 is turned off to stop the energy flow from capacitor C1 to patient 110.

For the second phase, reed relays RR1 and RR2 are opened, while reed relay RR3 is switched to pole P3 and reed relay RR4 is switched to pole P4, and switch SW1 is conductive. This allows current to flow from the positive terminal of capacitor C1 through pole P4 to patient 110, and back through pole P3 and switch SW1 to the negative terminal of capacitor C1, thus transferring most of the remaining energy from energy storage capacitor C1 to patient 110.

The advantage of the circuit of FIG. 6 is that the patient can be totally isolated from the circuit when all of the reed relay switches are off. This helps prevent the short circuiting of a defibrillation pulse from a second defibrillator. This is in contrast to the circuit of FIG. 3, where the relay switches RL1A and RLIB are either connected to the poles PL1 and PL3 or PL2 and PL4, respectively. The isolation of the reed relay switches of FIG. 6 also prevents leakage currents, which as described above can occur in an implementation such as that shown in FIG. 3. Another advantage of the isolation of the reed relay switches of FIG. 6, is that the preamplifier 120 is also isolated. For optimal preamplifier performance, it has been found that it is preferable to not have IGBT switches and energy storage capacitors connected to the preamplifier inputs, as would be the case in implementations such as those shown in FIGS. 3 and 5 when a preamplifier such as preamplifier 120 is used.

In summary, the present invention combines the use of at least one relay with a semiconductor switching element to achieve the phases of a multiphasic defibrillation pulse. In such a circuit, the semiconductor switching element is used to stop the energy flow between the phases of a multiphasic defibrillation pulse, while the relay is used to switch the effective polarity of the capacitor. As previously described, the control signal for the relay may be intentionally activated before the semiconductor switching element so as to cut down on the time that the circuit must wait between the two phases for the relay to finish switching. In the various embodiments of the present invention that have been illustrated, it has been shown that the relay can be: a double-pole, double-throw relay; two single-pole, double-throw relays with diodes designed to prevent the short circuiting of a second defibrillator; or four reed relays designed to allow the patient to be totally isolated from the defibrillator when it is not discharging. Other embodiments may also be envisioned while still maintaining the same general inventive combination of a semiconductor switching element and a relay element. For example, a relay similar to the double-pole, double-throw relay could be used which has a third pole position that is electrically isolated for purposes of standing off a defibrillation pulse from a second defibrillator. The relays may also be replaced by any similarly inexpensive non-semiconductor switching elements. Also, the IGBT or similar switching elements could be comprised of several switches and may be placed anywhere along the circuit path between the energy storage capacitor and the patient, such that it is capable of stopping the current flow between the phases of the multiphasic defibrillation pulse.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. In an external defibrillator for applying a multiphasic defibrillation pulse to a patient, said external defibrillator including an energy storage capacitor having first and second leads, said external defibrillator also having first and second output terminals for applying a biphasic defibrillation pulse to a patient when said first and second output terminals are coupled to a patient, said external defibrillator also including an output circuit for switchably coupling the energy storage capacitor to the first and second output terminals, said external defibrillator also including a control circuit for controlling the operation of said output circuit, the improvement comprising an improved defibrillator with an improved output circuit and an improved control circuit, said improved output circuit comprising:

(a) a switching element coupled between the energy storage capacitor and the output terminals, said switching element being configured to stop the flow of energy between the energy storage capacitor and the output terminals in order to end the first phase of a multiphasic defibrillation pulse;

(b) a non-semiconductor relay circuit coupled between the energy storage capacitor and the output terminals; and said improved control circuit controlling the non-semiconductor relay circuit and the switching element such that:

(i) the non-semiconductor relay circuit is placed in a first configuration and the switching element is placed in a conducting state for a first period to electrically couple the first lead of the energy storage capacitor to the first output terminal and to also electrically couple the second lead of the energy storage capacitor to the second output terminal so as to complete a circuit path between the energy storage capacitor and the first and second output terminals when the first and second output terminals are coupled to a patient, so as to conduct energy from the energy storage capacitor to the patient in the form of a first phase of a multiphasic defibrillation pulse; and (ii) the non-semiconductor relay circuit is placed in a second configuration and the switching element is placed in a conducting state for a second period to electrically couple the first lead of the energy storage capacitor to the second output terminal and to also electrically couple the second lead of the energy storage capacitor to the first output terminal to complete a circuit path between the energy storage capacitor and the first and second output terminals when the first and second output terminals are coupled to a patient, so as to conduct energy from the energy storage capacitor to the patient in the form of a second phase of a multiphasic defibrillation pulse.

2. The improvement of claim 1, wherein the non-semiconductor relay circuit comprises a double-pole, double-throw relay that has first and second relay switches, the first and second relay switches each having a first position and a second position.

3. The improvement of claim 2, wherein when the switching element is placed in a conducting state, the first relay switch of the double-pole, double-throw relay in the first position electrically couples the first output terminal to the first lead of the energy storage capacitor, and in the second position electrically couples the first output terminal to the second lead of the energy storage capacitor, and the second relay switch of the double-pole, double-throw relay in the first position electrically couples the second output terminal to the second lead of the energy storage capacitor and in the second position electrically couples the second output terminal to the first lead of the energy storage capacitor.

4. The improvement of claim 1, wherein the non-semiconductor relay circuit comprises a first single-pole, double-throw relay, and a second single-pole, double-throw relay, the first and second single-pole, double-throw relays each having a first position and a second position.

5. The improvement of claim 4, wherein when the switching element is placed in a conducting state, the first single-pole, double-throw relay in the first position electrically couples the first output terminal to the second lead of the energy storage capacitor and in the second position electrically couples the first output terminal to the first lead of the energy storage capacitor, and the second single-pole, double-throw relay in the first position electrically couples the second output terminal to the second lead of the energy storage capacitor and in the second position electrically couples the second output terminal to the first lead of the energy storage capacitor.

6. The improvement of claim 5, wherein in the normally closed resting position, the first single-pole, double-throw relay is in the first position, and the second single-pole, double-throw relay is also in the first position, and during the first phase of a multiphasic defibrillation pulse, the control circuit places the first single-pole, double-throw relay in the second position, and places the second single-pole, double-throw relay in the first position, and during the second phase of a multiphasic defibrillation pulse, the control circuit places the first single-pole, double-throw relay in the first position, and also places the second single-pole, double-throw relay in the second position.

7. The improvement of claim 6, wherein when the first single-pole, double-throw relay is in its first position, a diode is coupled between the first output terminal and the energy storage capacitor, and when the second single-pole, doublethrow relay is in its first position, a diode is coupled between the second output terminal and the energy storage capacitor, the diodes being capable of standing off the voltage of a defibrillation pulse applied from a second defibrillator.

8. The improvement of claim 1, wherein the non-semiconductor relay circuit comprises first, second, third, and fourth reed relays.

9. The improvement of claim 8, wherein the first reed relay is coupled between the first output terminal and the first lead of the energy storage capacitor, and the second reed relay is coupled between the second output terminal and the second lead of the energy storage capacitor, and the third reed relay is coupled between the first output terminal and the second lead of the energy storage capacitor, and the fourth reed relay is coupled between the second output terminal and the first lead of the energy storage capacitor.

10. The improvement of claim 9, wherein when no control signals are provided to the first, second, third, and fourth reed relays, the first, second, third, and fourth reed relays are open such that the patient is electronically isolated from the output circuit.

11. The improvement of claim 1, wherein the switching element is an IGBT switching element.

12. The improvement of claim 11, wherein the IGBT switching element comprises at least one IGBT switch.

13. The improvement of claim 1, wherein the non-semiconductor relay circuit comprises a plurality of relay switches, and the improved control circuit controls the plurality of relay switches and the switching element with control signals, the timing of at least one of the control signals for one of the relay switches being activated prior to the control signal for the switching element, so as to reduce a delay between the time when the relay switch and the switching element respond to the control signals.

14. An external defibrillator with an output circuit for conducting current from an energy storage device to a pair of output terminals when the output terminals are coupled to a patient, the current being conducted to the patient in the form of a multiphasic defibrillation pulse, the output circuit comprising:

(a) a switching element coupled between the energy storage device and the pair of output terminals, the switching element being capable of stopping the flow of current from the energy storage device to the output terminals in order to end the first phase of a multiphasic defibrillation pulse; and (b) a relay circuit including at least one non-semiconductor relay element coupled between the energy storage device and the output terminals, the at least one non-semiconductor relay element being operable to switch between at least two positions, the non-semiconductor relay element being switched to a first position when a patient is coupled to the defibrillator in order to conduct current from the energy storage device to the patient in the form of a first phase of a multiphasic defibrillation pulse, the non-semiconductor relay element being switched to a second position while the patient is coupled to the defibrillator in order to conduct current from the energy storage device to the patient in the form of a second phase of a multiphasic defibrillation pulse.

15. The output circuit of claim 14, wherein the relay circuit comprises a double-pole, double-throw relay.

16. The output circuit of claim 14, wherein the relay circuit comprises two single-pole, double-throw relays.

17. The output circuit of claim 14, wherein the relay circuit comprises four reed relays.

18. The output circuit of claim 14, wherein the defibrillator includes a control circuit for controlling the switching element and the non-semiconductor relay element of the output circuit with control signals, the control circuit activating at least one of the control signals for the non-semiconductor relay element prior to activating at least one of the control signals for the switching element so as to reduce the delay between when the switching element and the relay element respond to the control signals.

19. In an external defibrillator for applying a multiphasic defibrillation pulse to a patient, said external defibrillator including an energy storage capacitor having first and second leads, said external defibrillator also having first and second output terminals for applying a multiphasic defibrillation pulse to a patient when said first and second output terminals are coupled to a patient, said external defibrillator also including an output circuit for switchably coupling the energy storage capacitor to the first and second output terminals, said external defibrillator also including a control circuit for controlling the operation of said output circuit, the improvement comprising an improved defibrillator with an improved output circuit and an improved control circuit, said improved output circuit comprising:

(a) a switching element coupled between the energy storage capacitor and the output terminals, said switching element being capable of stopping the flow of energy between the energy storage capacitor and the output terminals in order to end the first phase of a multiphasic defibrillation pulse;

(b) a plurality of relay switches coupled between the energy storage capacitor and the output terminals, the plurality of relay switches in a first set of positions coupling the first lead of the energy storage capacitor to the first output terminal and the second lead of the energy storage capacitor to the second output terminal, and the plurality of relay switches in a second set of positions coupling the first lead of the energy storage capacitor to the second output terminal and coupling the second lead of the energy storage capacitor to the first output terminal; and said improved control circuit generating relay control signals to control the plurality of relay switches and also generating switching control signals to control the switching element, said improved control circuit generating at least one of said relay control signals prior to generating at least one of said switching control signals so as to reduce the delay between when the switching element and the relay switch respond to the control signals.

20. The improvement of claim 19, wherein the improved control circuit generates the at least one relay control signal at a fixed time before generating the at least one switching control signal, such that the time between the phases of the multiphasic defibrillation pulse is reduced to less than 5 milliseconds.

21. A method for operating an external defbrillator to apply a biphasic defibrillation pulse to a patient, the defibrillator including an energy storage device, a switching element, a non-semiconductor relay circuit, and a pair of output terminals for coupling to a patient, the method comprising:

(a) placing the switching element in a conducting state and placing the non-semiconductor relay circuit in a first configuration so as to conduct the first phase of a multiphasic defibrillation pulse from the energy storage device to a patient;

(b) placing the switching element in a non-conducting state so as to stop the flow of current from the energy storage device to the patient and thereby end the first phase of the multiphasic defibrillation pulse; and (c) placing the switching element in a conducting state and placing the non-semiconductor relay circuit in a second configuration so as to conduct the second phase of a multiphasic defibrillation pulse from the energy storage device to the patient.

22. The method of claim 21, wherein the switching element is a semiconductor switching element with a gate, and the steps of making the semiconductor switching element conducting are accomplished by applying a voltage to the gate.

23. An external defibrillator with an output circuit for conducting current from an energy storage device to a pair of output terminals when the output terminals are coupled to a patient, the current being conducted to the patient in the from of a multiphasic defibrillation pulse, the output circuit comprising:

(a) switching means coupled between the energy storage device and the pair of output terminals, the switching means being capable of stopping the flow of current from the energy storage device to the output terminals in order to end the first phase of the multiphasic defibrillation pulse; and (b) non-semiconductor relay means coupled between the energy storage device and the output terminals, the non-semiconductor relay means being operable to switch between at least two configurations, the non-semiconductor relay means in a first configuration conducting current from the energy storage device to the patient in the form of a first phase of a multiphasic defibrillation pulse, the non-semiconductor relay means in a second configuration conducting current from the energy storage device to the patient in the form of a second phase of a multiphasic defibrillation pulse.

24. An external defibrillator with an output circuit for conducting current from an energy storage device to a pair of output terminals when the output terminals are coupled to a patient, the current being conducted to the patient in the form of a multiphasic defibrillation pulse, the output circuit comprising:

(a) semiconductor switching means coupled between the energy storage device and the pair of output terminals, the semiconductor switching means being capable of stopping the flow of current from the energy storage device to the output terminals in order to end the first phase of the multiphasic defibrillation pulse; and (b) a plurality of non-semiconductor switches coupled between the energy storage device and the output terminals, the plurality of non-semiconductor switches being operable to switch between at least two configurations, the plurality of non-semiconductor switches in a first configuration conducting current from the energy storage device to the patient in the form of a first phase of a multiphasic defibrillation pulse, the plurality of non-semiconductor switches in a second configuration conducting current from the energy storage device to the patient in the form of a second phase of a multiphasic defibrillation pulse.

25. A method for operating an external defibrillator to apply a multiphasic defibrillation pulse to a patient, the defibrillator including an energy storage device, a non-semiconductor relay circuit, and first and second output terminals for coupling to a patient, the method comprising:

(a) placing the non-semiconductor relay circuit in a first configuration so as to conduct a first phase of a multiphasic defibrillation pulse from the energy storage device to a patient;

(b) the non-semiconductor relay circuit in the first configuration controlling the direction of current flow during the first phase of the multiphasic defibrillation pulse such that current flows through the patent in a direction from the first output terminal to the second output terminal;

(c) placing the non-semiconductor relay circuit in a second configuration so as to conduct a second phase of the multiphasic defibrillation pulse from the energy storage device to the patient, and (d) the non-semiconductor relay circuit in the second configuration controlling the direction of current flow during the second phase of the multiphasic defibrillation pulse such that current flows through the patient in a direction from the second output terminal to the first output terminal.

26. The method of claim 25, wherein the non-semiconductor relay circuit comprises a plurality of non-semiconductor relay switches.

27. An external defibrillator with an output circuit for conducting current from an energy storage device to first and second output terminals when the output terminals are coupled to a patient, the current being conducted to the patient in the form of a multiphasic defibrillation pulse, the output circuit comprising:

(a) non-semiconductor relay means coupled between the energy storage device and the output terminals, the non-semiconductor relay means being operable to switch between at least two configurations;

(b) the non-semiconductor relay means in a first configuration conducting current from the energy storage device to the patient in the form of a first phase of a multiphasic defibrillation pulse, the current flow during the first phase of the multiphasic defibrillation pulse being controlled by the non-semiconductor relay means to be in a direction from the first output terminal to the second output terminal; and (c) the non-semiconductor relay means in a second configuration conducting current from the energy storage device to the patient in the form of a second phase of a multiphasic defibrillation pulse, the current flow during the second phase of the multiphasic defibrillation pulse being controlled by the non-semiconductor relay means to be in a direction from the second output terminal to the first output terminal.

28. The external defibrillator of claim 23 wherein the non-semiconductor relay means comprises a plurality of non-semiconductor relay switches.

* * * * *